United States Patent
Mancine et al.

(10) Patent No.: US 11,240,182 B2
(45) Date of Patent: *Feb. 1, 2022

(54) SYSTEMS AND METHODS FOR AUTOMATED AND CENTRALIZED REAL-TIME EVENT DETECTION AND COMMUNICATION

(71) Applicant: TeleTracking Technologies, Inc., Pittsburgh, PA (US)

(72) Inventors: Nathan Mancine, Cranberry Township, PA (US); John Rovnan, Gibsonia, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/862,994

(22) Filed: Apr. 30, 2020

(65) Prior Publication Data

US 2020/0259769 A1    Aug. 13, 2020

Related U.S. Application Data

(63) Continuation of application No. 16/214,427, filed on Dec. 10, 2018, now Pat. No. 10,652,176, which is a
(Continued)

(51) Int. Cl.
*H04L 12/58* (2006.01)
*G16H 40/20* (2018.01)
*H04L 29/08* (2006.01)

(52) U.S. Cl.
CPC .............. *H04L 51/04* (2013.01); *G16H 40/20* (2018.01); *H04L 67/18* (2013.01); *H04L 67/327* (2013.01)

(58) Field of Classification Search
CPC ....... H04L 51/04; H04L 67/18; H04L 67/327; G16H 40/20; G16H 40/63; G16H 10/60;
(Continued)

(56) References Cited

U.S. PATENT DOCUMENTS 7,613,620 B2 * 11/2009 Salwan ................... G16H 10/60
                                                                        705/2
8,296,162 B1 * 10/2012 Horn ...................... G06Q 10/10
                                                                        705/2
(Continued)

FOREIGN PATENT DOCUMENTS

EP              1914650 A2       4/2008

OTHER PUBLICATIONS

U.S. Non-Final Rejection dated Dec. 28, 2017 for U.S. Appl. No. 15/360,679, filed Nov. 23, 2016.
(Continued)

*Primary Examiner* — Alina A Boutah
(74) *Attorney, Agent, or Firm* — Ference & Associates LLC

(57) ABSTRACT

Centralized hospital communication system and methods are provided for event monitoring and notification. In some embodiments, consistent with the present embodiments, a centralized hospital communication server is disclosed. The centralized hospital communication server may include a memory storing instructions, and at least one processor configured to execute the stored instructions to: receive, from a networked device, event information indicative of an event, the event information including at least one personal attribute of a first individual associated with the event; search a network database for information associated with at least one location within a hospital, the first location information including at least one location attribute; identify, based on the received event information and the received
(Continued)

first location information, a selected location for the first individual associated with the event; and automatically generate and transmit at least one electronic communication to a first electronic device associated with the selected location.

20 Claims, 11 Drawing Sheets

Related U.S. Application Data continuation of application No. 15/360,679, filed on Nov. 23, 2016, now Pat. No. 10,153,994.

(60) Provisional application No. 62/259,344, filed on Nov. 24, 2015.

(58) Field of Classification Search
CPC ........ G16H 80/00; G06Q 10/10; G06Q 10/06; H04W 4/12
USPC .............................. 705/2, 3, 5, 6, 7.14, 7.22
See application file for complete search history.

(56) References Cited

U.S. PATENT DOCUMENTS

| Patent/Publication | Date | Inventor | Classification |
|---|---|---|---|
| 8,560,580 B1* | 10/2013 | Nacey | G06F 21/31 707/825 |
| 8,732,573 B2* | 5/2014 | Nacey | G16H 40/20 715/251 |
| 8,930,223 B2* | 1/2015 | Friedlander | G06F 19/00 705/3 |
| 2003/0074222 A1* | 4/2003 | Rosow | G16H 10/60 705/2 |
| 2005/0080650 A1* | 4/2005 | Noel | G16H 20/60 705/2 |
| 2006/0004605 A1* | 1/2006 | Donoghue | G16H 10/60 705/2 |
| 2006/0143045 A1* | 6/2006 | Nacey | G16H 40/20 705/2 |
| 2006/0229918 A1* | 10/2006 | Fotsch | G16H 10/60 705/3 |
| 2006/0247948 A1* | 11/2006 | Ellis | G16H 40/20 705/2 |
| 2007/0239484 A1* | 10/2007 | Arond | G16H 40/20 705/2 |
| 2008/0027754 A1* | 1/2008 | Auker | G16H 40/63 705/2 |
| 2008/0126126 A1* | 5/2008 | Ballai | G08B 21/22 705/2 |
| 2009/0118595 A1* | 5/2009 | Greiner | A61B 5/0006 600/301 |
| 2009/0243833 A1* | 10/2009 | Huang | G16H 10/65 340/505 |
| 2011/0208541 A1* | 8/2011 | Wilson | A61G 12/00 705/3 |
| 2012/0112883 A1* | 5/2012 | Wallace | G16H 40/67 340/10.1 |
| 2012/0116793 A1* | 5/2012 | Barber-Mingo | G16H 40/20 705/2 |
| 2012/0116803 A1* | 5/2012 | Reid | G16H 40/20 705/2 |
| 2013/0041680 A1* | 2/2013 | Klein | G16H 10/40 705/2 |
| 2013/0090130 A1* | 4/2013 | Burrell | H04W 4/21 455/456.1 |
| 2013/0108035 A1* | 5/2013 | Lyman | H04L 51/04 379/218.02 |
| 2013/0304485 A1* | 11/2013 | Khan | G16H 40/67 705/2 |
| 2014/0108035 A1* | 4/2014 | Akbay | G06Q 10/0631 705/2 |
| 2015/0100333 A1* | 4/2015 | Fitzgerald | G16H 40/67 705/2 |
| 2015/0116112 A1* | 4/2015 | Flinsenberg | G16H 40/20 340/539.11 |
| 2015/0302539 A1* | 10/2015 | Mazar | G16H 40/20 705/3 |
| 2016/0072681 A1* | 3/2016 | Rawat | G06F 3/04847 715/736 |
| 2016/0132650 A1* | 5/2016 | Kejriwal | G16H 40/20 705/2 |
| 2016/0140299 A1* | 5/2016 | Al Harbi | G06F 19/00 705/2 |
| 2016/0147972 A1* | 5/2016 | Mancine | G16H 80/00 705/3 |
| 2016/0300178 A1* | 10/2016 | Perry | G06Q 10/063116 |
| 2016/0350489 A1* | 12/2016 | Ribble | G16H 40/20 |
| 2016/0350499 A1* | 12/2016 | Anjomshoa | G16H 40/20 |
| 2016/0371441 A1* | 12/2016 | Day | G16H 40/20 |
| 2017/0017758 A1* | 1/2017 | McReynolds | G16H 20/10 |

OTHER PUBLICATIONS

U.S. Final Rejection dated Aug. 16, 2017 for U.S. Appl. No. 15/360,679, filed Nov. 23, 2016.
U.S. Final Rejection dated Mar. 21, 2017 for U.S. Appl. No. 15/360,679, filed Nov. 23, 2016.

* cited by examiner

SYSTEMS AND METHODS FOR AUTOMATED AND CENTRALIZED REAL-TIME EVENT DETECTION AND COMMUNICATION

PRIORITY CLAIM

This application is a continuation of U.S. patent application Ser. No. 16/214,427, filed on Dec. 10, 2018, which is a continuation of U.S. patent application Ser. No. 15/360,679, filed on Nov. 23, 2016, which issued on Dec. 11, 2018 as U.S. Pat. No. 10,153,994, which claims priority from U.S. Provisional Application No. 62/259,344, filed Nov. 24, 2015. The disclosures of the above-referenced applications are expressly incorporated herein by reference in their entireties.

TECHNICAL FIELD

The present disclosure is directed to the technical field of centralized event detection and communications. More particularly, disclosed embodiments are directed to centralized server-based communication systems for generating automated electronic messages in a facility based on detected events.

BACKGROUND

Modern hospitals treat hundreds of patients every day. When a patient arrives, their condition and needs must be evaluated and addressed quickly, often requiring the coordination and communication of multiple departments in the hospital. In many situations, the incoming patient must be placed in the proper area of the hospital, and sometimes the patient must meet with multiple physicians located in different hospital units or facilities for appointments scheduled based on the patient condition and also when emergencies arise, requiring transport from one area of the hospital to another or to other hospitals/facilities. Accomplishing these tasks requires frequent and constant exchange of data and information throughout the hospital and between multiple hospitals.

Traditional communication techniques for event detection and communication in such environments are based upon outdated communication technologies, resulting in overloaded systems that are slow, error-prone, and do not provide facility-wide communication using a centralized system. Indeed, traditional techniques usually rely upon multiple disparate systems, which may not integrate and exchange information. Some traditional techniques involve manual reporting of an event and/or manual requests for transportation, usually through phone calls between individuals in the facility. At the scale of modern hospital operations, traditional systems usually result in overloaded telephone lines, missed requests.

In view of the technical deficiencies of current systems discussed above, there is a need for improved systems and methods centralized real-time event detection and communication.

SUMMARY

Disclosed embodiments relate to systems and methods for automated and centralized real-time event detection and communication. In some embodiments, events can include patient transfers, placement, and other activities performed by the system. Disclosed embodiments may provide for monitoring a plurality of parameters, schedules, milestones, and events associated with a patient visit, from the patient intake process through to patient discharge and beyond. In some embodiments, event information is received from a network device. Event information can include, for example, a status of one or more hospital beds monitored for occupancy, cleanliness, and maintenance. In some embodiments, the system automatically assigns a patient bed based on attributes about the patient, attributes about the hospital bed, and scheduling and availability. In some embodiments, the system automatically coordinates admission requests from other hospitals in communication with the hospital, and generates admission requests to send patients to other hospitals based on the needs of the patient. In some embodiments, the system provides a bidirectional networked interface to one or more individuals outside the hospital network, such as referring physicians, specialists, and other interested parties, to allow the exchange of information associated with a patient.

Disclosed embodiments address the technical problems discussed above through the use of a centralized server that dynamically and automatically generates requests for information from computerized sources and networked databases located throughout the facility to obtain data such as event information and location information. Disclosed embodiments also utilize sensor devices located throughout the facility, and automate the generation of electronic communications to electronic devices associated with a detected event or required action based on the detected event. Thus, the disclosed embodiments provide a combination and arrangement of computerized hardware in conjunction with ordered combinations of steps in a particular application.

The disclosed embodiments may provide improved communication systems between departments in a facility, and provide intelligent automated communications associated with event detection such as triggered or scheduled events, staff transition, and patient handoff times.

Consistent with the present embodiments, a centralized hospital communication server for event monitoring and notification is disclosed. The centralized hospital communication server may include a memory storing instructions and at least one processor configured to execute the stored instructions to: receive, from a networked device, event information indicative of an event, the event information including at least one personal attribute of a first individual associated with the event; search a network database for information associated with at least one location within a hospital, the first location information including at least one location attribute; identify, based on the received event information and the received first location information, a selected location for the first individual associated with the event; and automatically generate and transmit at least one electronic communication to a first electronic device associated with the selected location. Consistent with the present embodiments, a centralized hospital communication method for event monitoring and notification being performed by a centralized communication server is disclosed. The centralized hospital communication method may include: receiving, from a networked device, event information indicative of an event, the event information including at least one personal attribute of a first individual associated with the event; searching a network database for information associated with at least one location within a hospital, the first location information including at least one location attribute; identifying, based on the received event information and the received first location information, a selected location for the first individual associated with the event; and automatically generating and transmitting at least one electronic communication to a first electronic device associated with the selected location.

Consistent with other disclosed embodiments, a non-transitory computer-readable medium may store program instructions, which are executed by at least one processor device and cause a central communication server to perform operations for centralized event monitoring and notification communications.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings:

FIG. 7 is an illustration of an example of a census user interface, consistent with embodiments of the present disclosure;

FIG. 8 is an illustration of an example of a bed request user interface, consistent with embodiments of the present disclosure;

FIG. 9 is an illustration of an example of a bed attribute user interface, consistent with embodiments of the present disclosure;

FIG. 10 is an illustration of an example of a placement request user interface, consistent with embodiments of the present disclosure;

FIG. 11 is an illustration of an example of a bed assignment user interface, consistent with embodiments of the present disclosure.

DETAILED DESCRIPTION OF EXEMPLARY EMBODIMENTS

Reference will now be made in detail to exemplary embodiments, examples of which are illustrated in the accompanying drawings and disclosed herein. Wherever convenient, the same reference numbers will be used throughout the drawings to refer to the same or like parts.

Figure 1:
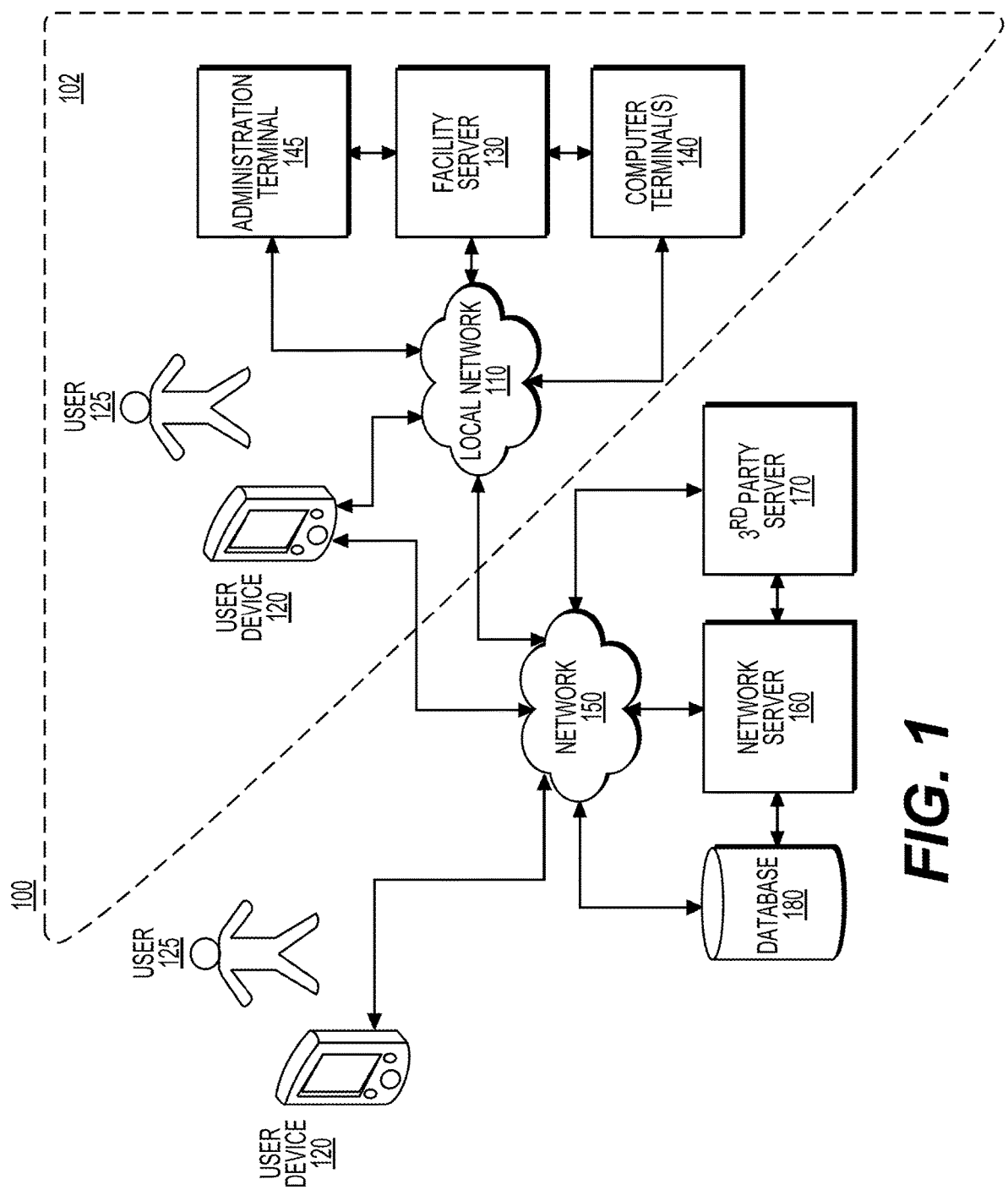
FIG. 1 depicts an example of a system environment for placing patients within a hospital, consistent with embodiments of the present disclosure.

FIG. 1 shows a diagram of a patient placement and workflow management system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, patient placement and workflow management system 100 may include a facility server 130, a computer terminal 140, an administration terminal 145, one or more user devices 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and at least one user device 120 may be physically disposed within a facility such as a hospital or office building (i.e. as facility system 102) while at least one user device 120, network 150, network server 160, third party server 170, and database 180 may be external to the workplace. Other components known to one of ordinary skill in the art may be included in system 100 to perform tasks consistent with the disclosed embodiments. For example, in some embodiments, facility system 102 may include one or more sensor devices located throughout the facility to monitor one or more conditions such as occupancy, temperature, humidity, proximity, and other parameters indicative of a status or condition of a bed, room, area, equipment, or supplies. Additionally, in some embodiments facility system 102 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, or any other display. In some embodiments, computer terminal 140 may be associated with a particular room in a facility, such as a particular patient room, hotel room, conference room, or any other type of room. Thus, a message received from a computer terminal 140 may automatically associate the message with the room in which computer terminal 140 is installed.

Administrator terminal 145 may include computer system or device associated with a user 125 that manages or oversees a portion of facility system 102. For example, administrator terminal 145 may comprise a computer system located at a head nurse station, a housekeeping manager's office, or any other department manager's office or station.

Users 125 may be one or more individuals, such as hospital employees and caregivers, associated with the patient. Users 125 may operate computer terminal 140, user devices 120, and/or another computer (not shown) to interact with system 100. Users 125 may be individuals located within and/or outside of the facility system 102. For example, users 125 may include physicians and nurses within the facility responsible for transferring the patients to different units. Users 125 may also include one or more individuals who are responsible for responding to task requests, such as cleaning and transportation of the patients. Users 125 may also include individuals outside of facility system 102, such as people with personal relationships with the patients (e.g. family members) and referring individuals (e.g. outside physicians and medics).

System 100 may be customizable and provide individualized access for each of the users 125. For example, only certain users 125, such as physicians and nurses, may be allowed to generate transfer requests. In some embodiments, one or more users 125, such as the patient's primary physician, may be required to authorize all requests. Users 125 solely responsible for specific tasks may have access limited to perform their responsibilities. It is also contemplated that some users 125, such as family members, may have read-only access.

User devices 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, a user device 120 may be a computer system or mobile computer device that is operated by user 125. In some embodiments, a user device 120 may be associated with a particular individual such as user 125, such that messages and/or task assignments directed toward user 125 are sent to user device 120.

In some embodiments, user device 120 may communicate with facility server 130 and/or network server 160 via direct wireless communication links (not shown), or via a combination of one or more of local network 110 and/or network 150.

Facility server 130 may be operated by a facility such as a hospital. Facility server 130 may enable communication within a computer-based system including computer system components such as desktop computers, workstations, tablets, hand held computing devices, memory devices, and/or internal network(s) connecting the components. Thus, in some embodiments facility server 130 may operate as a centralized hub or station for receiving and processing data associated with disclosed methods and techniques, and for generating and sending transmissions associated with disclosed methods and techniques.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™' Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
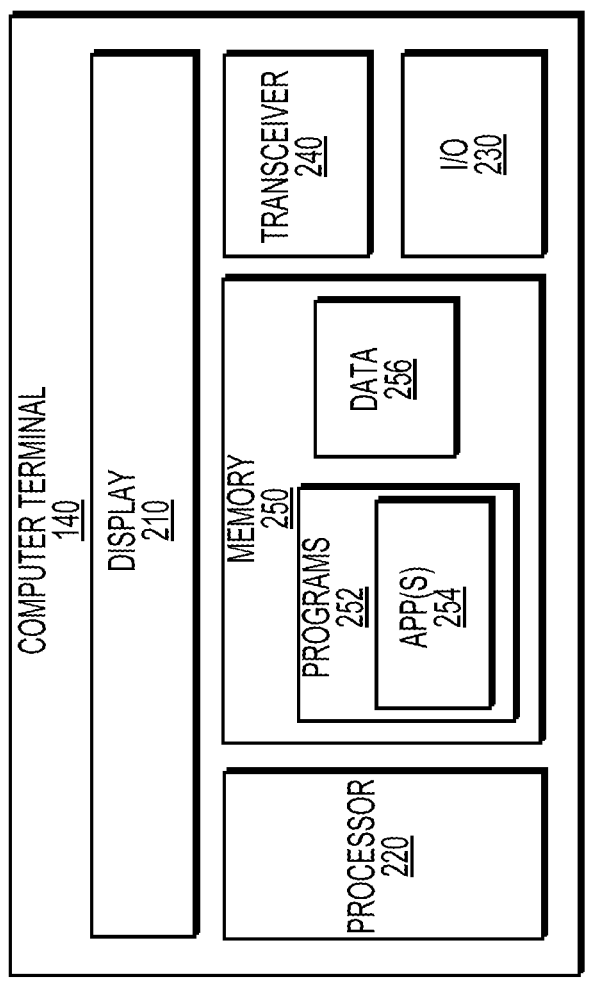
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, tape, optical, removable, non-removable, or other type of storage device or tangible (i.e., non-transitory) computer-readable medium that stores one or more program(s) 252, such as app(s) 254, and data 256. Data 256 may include, for example, patient information, user information, task information, and display settings and preferences. In some embodiments, data 256 may include one or more rule sets for prioritizing information and placing individual patients.

Program(s) 252 may include operating systems (not shown) that perform known operating system functions when executed by one or more processors. By way of example, the operating systems may include Microsoft Windows™, Unix™ Linux™ Apple™ operating systems, Personal Digital Assistant (PDA) type operating systems, such as Microsoft CE™ or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a patient placement and workflow management app, which when executed causes computer terminal 140 to perform processes related to managing, prioritizing, and scheduling patient information and tasks. For example, app(s) 254 may configure computer terminal 140 to perform operations including receiving input of patient transfer requests, displaying patient information, monitoring patient statuses, assigning tasks to employees, displaying employee assignments, and monitoring task statuses.

Figure 3:
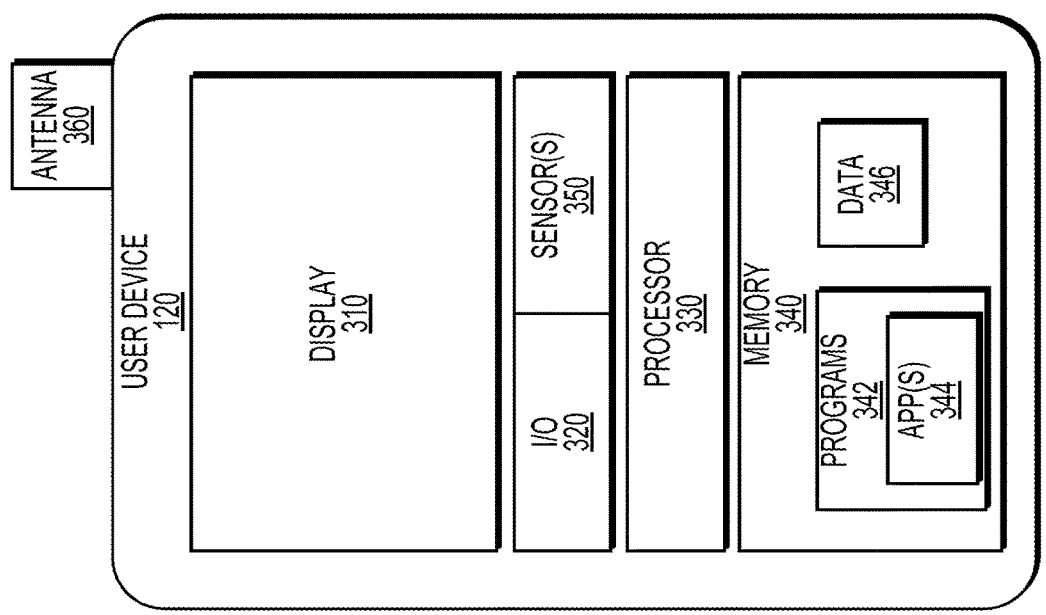
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
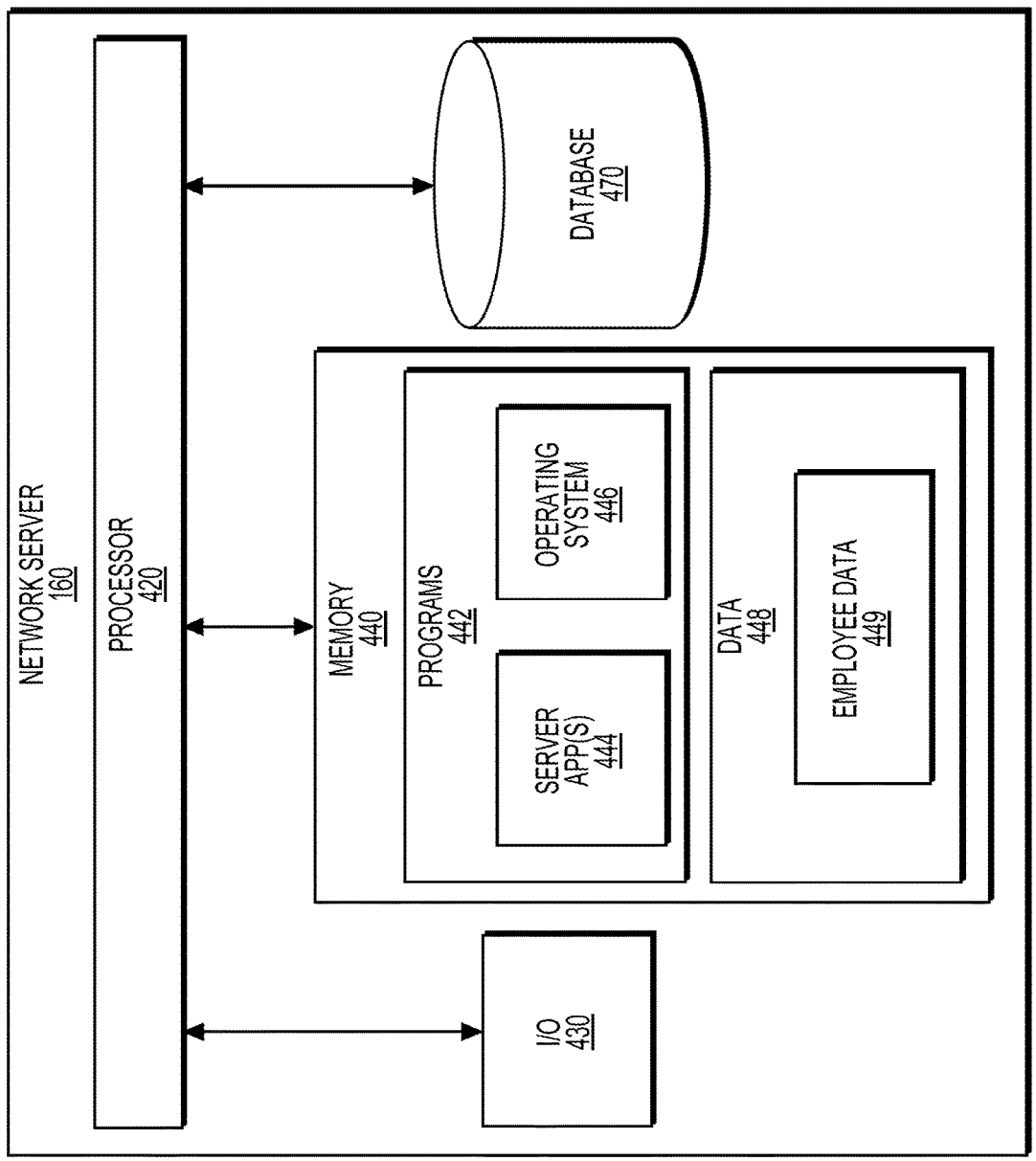
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure™ or Amazon Web Services. In such embodiments, network server 160 may include one or more distributed computer systems capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as transferring patients between facilities. Additionally, network server 160 may collect data from multiple units to evaluate performance times in different units, and improve the accuracy of expected completion times for different types of tasks using one or more data regression algorithms.

As shown in FIG. 4, network server 160 may include one or more processor(s) 420, input/output ("I/O") devices 430, memory 440 storing programs 442 (including, for example, server app(s) 444 and operating system 446) and data 448, and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more user 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of patient information, request patient transfers, monitor patient transfers, assign tasks to users 125, and display user task assignments In some embodiments, memory 440 may store data 448 including data associated with patients, units, employees, tasks, assets, assignment algorithms, and any other data related to the disclosed embodiments. For example, data 448 may include one or more entries including information pertaining to patients including identification, bed assignment, personal traits, previous conditions, priorities, and preferences. Data 448 may also include one or more entries pertaining to users 125 such as occupation, association with patients, responsibilities, and request statuses. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
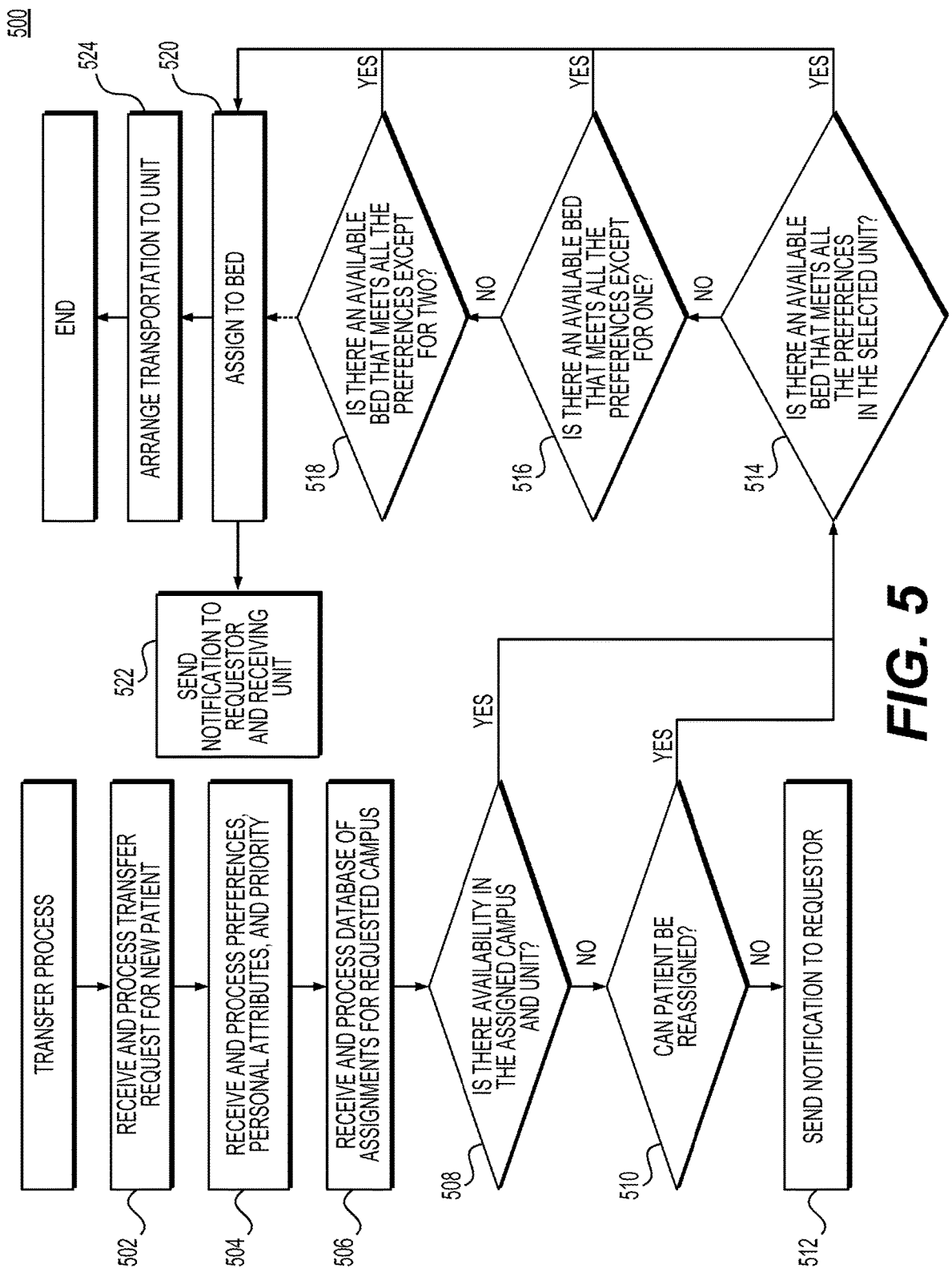
FIG. 5 is a flowchart of an example of a process for detecting events within a facility and communicating information, consistent with embodiments of the present disclosure.

FIG. 5 shows a flowchart of exemplary process 500 for detecting events within a facility and communicating information. Process 500 may provide the advantage of getting patients into the right level and location of care as quickly as possible. Process 500 may also advantageously distinguish critical from non-critical criteria to efficiently place the patient in the most comfortable setting possible. Process 500 is described herein as performed primarily by network server 160, however in some embodiments, facility server 130, computer terminal 140, administration terminal 145, user device 120, and/or third party server 170 may perform one or more steps of process 500.

Process 500 may begin in step 502 when network server 160 detects an event within the facility. In some embodiments, network server 160 may detect an event in response to receipt of monitoring information for one or more networked devices. In some embodiments, monitoring information may comprise sensor data collected by one or more networked sensor devices. In some embodiments, monitoring information may include a task request from a terminal such as computer terminal 140, administration terminal 145, and/or user device 120. In some embodiments, requests may include a text message, email, communication from app 254 or 344, or other written request from any electronic device in communication with network server 160. In some embodiments, network server 160 may receive one or more requests via another interface, such as an interactive voice response (IVR) system, or touch-tone phone entry system. The requests may be provided in an interface having fields that are either critical or non-critical for patient placement. Network server 160 may also be provided with voice or character recognition software configured to extract information for inputs from other types of requests.

In step 504, network server 160 may receive additional inputs pertaining to the patient. The inputs may include information to supplement the information received in step 502, such as personal attributes, patient preferences, and isolation information. Personal attributes may include, for example, physiological data, gender, height, weight, age, mental health, physical health, mobility, personality, level of sedation, and/or any other physical or mental characteristic. Patient preferences may include, for example, bed size, bed firmness, bed adjustability, level of care, desired interaction with other patients, desired location relative to a nurse's station or a window, and/or any other special accommodations. The isolation information may include information relating to any transmittable disease, such as transmission type (e.g., airborne, contact, etc.) and organism (e.g., MRSA). Some inputs may be closely related such that network server 160 may have an auto-populate feature that fills a first input based on a second input. For example, in one embodiment, network server 160 may automatically alter the requested bed size based on a patient's height and weight. It is also contemplated that network server 160 may automatically generate a bed request closer to the nursing station and isolated from the general population when the patient is experiencing mental health issues associated with increased levels of care and/or privacy.

Network server 160 may also receive and/or determine the priority a priority level of one or more of the inputs. The priority of the inputs may be automatically determined based on the character of the inputs, and/or may be manually inputted by the user 125. The priority of the inputs may initially be defined by whether the input is either critical or not critical for patient placement. In some embodiments, the priority may be further defined according to the relative importance of each of the critical and non-critical inputs. In some embodiments, system 100 may store and utilize a predetermined hierarchy of importance for each input, to optimize bed placement. For example, with patients having a height and/or weight greater than a threshold, network server 160 may automatically make the bed size critical to the patient placement. As another example, a patient's desired bed size and firmness may be considered non-critical, and given less weight in comparison to critical inputs. In this example, network server 160 may consider the bed size and the bed firmness when placing the patient, but the features may not be necessary for proper placement.

In some embodiments, network server 160 may populate one or more inputs by retrieving patient information from database 180, or from any other memory associated with components of system 100. For example, network server 160 may access patient records, or personal attributes, including information pertaining to physical properties (e.g. height and weight), prior medical conditions, mental health, prior hospital visits, prior diagnoses, prior and current prescriptions, home address, and personal contacts. Based on the inputs of the referring physical, network server 160 may automatically update patient records. In some embodiments, if network server 160 detects an inconsistency between the input of step 504 and the retrieved patient records, network server 160 may provide a prompt to the referring physician to ensure accuracy of the updated information.

In some embodiments, steps 502 and 504 may be performed simultaneously such that the data fields may be inputted on the same user interface. In other embodiments, the data fields of steps 502 and 504 may be separated by tabs and/or inset menus. In some embodiments, network server 160 may not require input for every field presented in the user interface to process a placement request. For example, bed firmness may be a non-critical input, such that if the data field was left blank, network server 160 may place the patient without considering the firmness of the bed. By providing optional data fields, the patient placement process is streamlined for requests that are urgent or have little available information, and the patient placement process is highly configurable for requests with numerous available preferences and parameters.

In step 506, network server 160 may retrieve and process information pertaining to the requested hospital. The information may include detailed information of each unit of the hospital including, for example, the number and locations of occupied and unoccupied beds of each unit, and the status of the patients of each occupied bed. Specifically, the network server 160 may receive personal attributes of each of the patients (e.g. gender, age, and personality) along with the expected discharge of each of the patients. In some embodiments, available locations identified in one or more databases may include unoccupied bed locations, such as a room number and/or letter for a bed that is not currently associated with an admitted patient. Occupied beds as well as beds assigned to patients pending discharge may therefore be stored as unavailable locations. In some embodiments, unavailable locations may include an indication that they are expected to become available within a predetermined time period. The predetermined time period, for example, can be associated with the metrics calculated by the system associated with the store patient condition, patient progress through an itinerary generated in association with the patient condition, and stored metrics associated with a predetermined patient discharge process, and the patient's current status in the discharge process. In some embodiments, the predetermined time period may be associated with one or more scheduled events for cleaning or maintaining the unavailable location, and an expected completion time for the scheduled events. Network server 160 may also receive location attributes, for example, detailed information of each of the beds, including firmness, size, adjustability, bed type, capabilities, and attached monitoring and care equipment. Based on the detailed information about the hospital beds and current patients, network server 160 may generate a chart for one or more hospital units to provide a real-time status of the hospital's current capacity level and its available capacity. In some embodiments, one location attribute includes a real-time available capacity level of a respective location.

In some embodiments, step 506 may be performed concurrently with steps 502 and 504. For example, network server 160 may generate and display the chart to user 125 to allow manual assignment of a bed to a new patient without inputting any information. In some embodiments, after receiving a manual bed selection, process 500 may proceed directly to step 520, to assign the selected bed to the patient. In other embodiments, network server 160 may take into account the manual bed request, but still proceed to step 508 to optimize the patient placement based on other data inputs received with the bed selection.

In step 508, network server 160 may determine whether there are one or more available beds located in the requested unit of the requested hospital. The availability of the bed may be determined by whether the bed is either unoccupied or occupied by a patient with a pending or confirmed discharge. Network server 160 may also determine if at least one of the beds provides all of the critical preferences of steps 502 and 504. If such a bed is available in the requested unit ("yes" in step 508), process 500 may proceed to step 514, in which network server 160 further process the bed assignment. If no such bed is available in the assigned unit ("no" in step 508), process 500 may proceed to step 510, where network server 160 may attempt to reassign the patient to another unit and/or another hospital. Step 510 may be similar to step 508, in that network server 160 may attempt to reassign the patient based on critical preferences. However, step 510 may expand process 500 to other related and/or unrelated units of the same or other hospitals of the network. The inquiry of step 510 may be determined by a number of different determinations, such as the relatedness or the physical proximity to the requested unit. The order of reassigning the patient may have a number of different configurations. In some embodiments, network server 160 may be configured to first examine another unit of the same hospital, then network server 160 may be configured to examine similar units (e.g. units performing the same or related procedures) of different hospitals. In other embodiments, network server 160 may be configured to first examine similar units of different hospital, and then examine another unit of the requested hospital. This configuration of network server 160 may depend on the individual patient. For example, for patients who require specialized care that is only available at the requested hospital, network server 160 may be configured to first examine different units of the requested hospital. This configuration may also be favorable for patients who prefer the location of the requested hospital. For other patients who require a bed at a particular unit regardless of the hospital, network server 160 may be configured to examine units of other hospitals and may not even consider other units of the requested hospital.

If network server 160 is unable to reassign the patient ("no" in step 510), process 500 may proceed to step 512, where network server 160 automatically may send a notification to user 125 that the patient assignment is not available. In some embodiments, network server 160 may expedite bed cleaning to make a bed available. For example, network server 160 may notify selected user(s) 125 to indicate a bed cleaning assignment corresponding to the request. Network server 160 may, additionally or alternatively, suggest to the requesting user 125 changes in the preferences to get a bed placement in the requested unit or locations of other hospitals.

After one or more beds are found to have the critical preferences in steps 508-510, steps 514-518 may provide an iterative approach to optimize the bed assignment accordingly to the non-critical inputs. In steps 514-518, network server 160 may be configured to assign the patient to one of the beds selected in steps 508-510 based on the non-critical inputs such as preferences, personal attributes, and/or priorities of step 504. In one embodiment, network server 160 may assign the patient to the bed that meets the most inputted preferences and/or personal attributes. In this embodiment, it is also contemplated that network server 160 may weigh each of the preferences and/or personal attributes based on the inputted priority. In another embodiment, network server 160 may also be configured to only consider one or more of the preferences and/or personal attributes based on priority. For example, network server 160 may be configured to determine if any beds selected from steps 508-510 meet the non-critical input with the highest priority. If there is a single bed that meets that search query, the patient may be placed in that bed. If there is more than one bed that meets the non-critical input with the highest priority, network server 160 may query those beds to determine if any beds also meet the non-critical input with the second highest priority, and so on. If no bed of steps 508-510 meets the non-critical input with the highest priority, network server 160 may determine if any of the beds meet the non-critical input with the second highest priority, and so on.

Network server 160 may match the patient to the bed based on the preferences and/or personal attributes in any number of ways. For example, network server 160 may take into account an input of the desired bed type (e.g. firmness, size, adjustability) or physical location (e.g. proximity to a window or a nursing station). The network server 160 may also factor in the physical and/or personality traits of the patients in the occupied beds. It is contemplated that the network server 160 may be configured to place the patient proximate other patients with the same gender and/or age to optimize patient comfort. The network server 160 may also be configured to automatically place individuals proximate other patients with similar personality types. For example, network server 160 may be configured to place more outgoing individuals proximity to each other or in the same room. On the other hand, if the patient requests a quieter environment, the server 160 may place the patient accordingly. In some embodiments, network server 160 is configured to select an unavailable location when at least one location attribute for the unavailable location corresponds to the personal attribute. In yet other embodiments, network server 160 is configured to determine a priority of an individual based on at least one personal attribute, wherein the selected location is associated with the determined priority.

In some embodiments, network server 160 may employ one or more rule sets or algorithms to balance loads in different units of a facility, by In optimizing the work load of each department and/or hospital. For example, network server 160 may be configured to receive assignment and/or discharge data from database 180 for each department and/or hospital, and process the received data to assign the patient bed based on real-time department and/or hospital loads, to assign the hospital unit best positioned to receive and/or discharge the patient at the corresponding date and/or time. Load balancing may reduce delay involving the receipt and/or discharge of the patient.

Once a bed assignment is optimized according to steps 514-518, network server 160 may assign the patient to the optimal bed in step 520. Once the assignment is complete, network server 160 may automatically send a notification to user 125 and the receiving unit in step 522. Network server 160 may also update the database of bed assignments and arrange for transportation of the patient to the assigned unit in step 524.

Specifically, in step 524, network server 160 may notify selected users 125 of the task that needs to be performed. The selected users 125 may be determined based on a certain occupation, such as a nurse. The selected users 125 may also be determined based on known availability of the users 125. In this sense, network server 160 may query a database to determine which of the selected users 125 are on duty and which of the selected users are on-call. Network server 160 may also determine the geographic positioning of each of the selected users 125 to determine which selected user 125 is in the best position to complete the task. Network server 160 may automatically notify one or more of the selected users 125, via user device 120, with detailed comments or priority of the task. This notification may require acknowledgement or acceptance of the task. In some embodiments, server may determine that user 125 has acknowledged the task if user device 120 associated with the user 125 indicates that the user 125 has accessed or viewed the notification for the task. In some embodiments, network server 160 may determine that a user 125 has acknowledged the task based on an input received from the user 125 via user device 120. If there is no affirmative acknowledgment after a certain amount of time (e.g., about 5 minutes) passes, network server 160 may send a reminder notification to the selected users 125 to ensure receipt. If is no acceptance from the selected users 125, network server 160 may alter the determination of the selected users 125 and send additional notifications to other users 125 to ensure that the task is completed.

Figure 6:
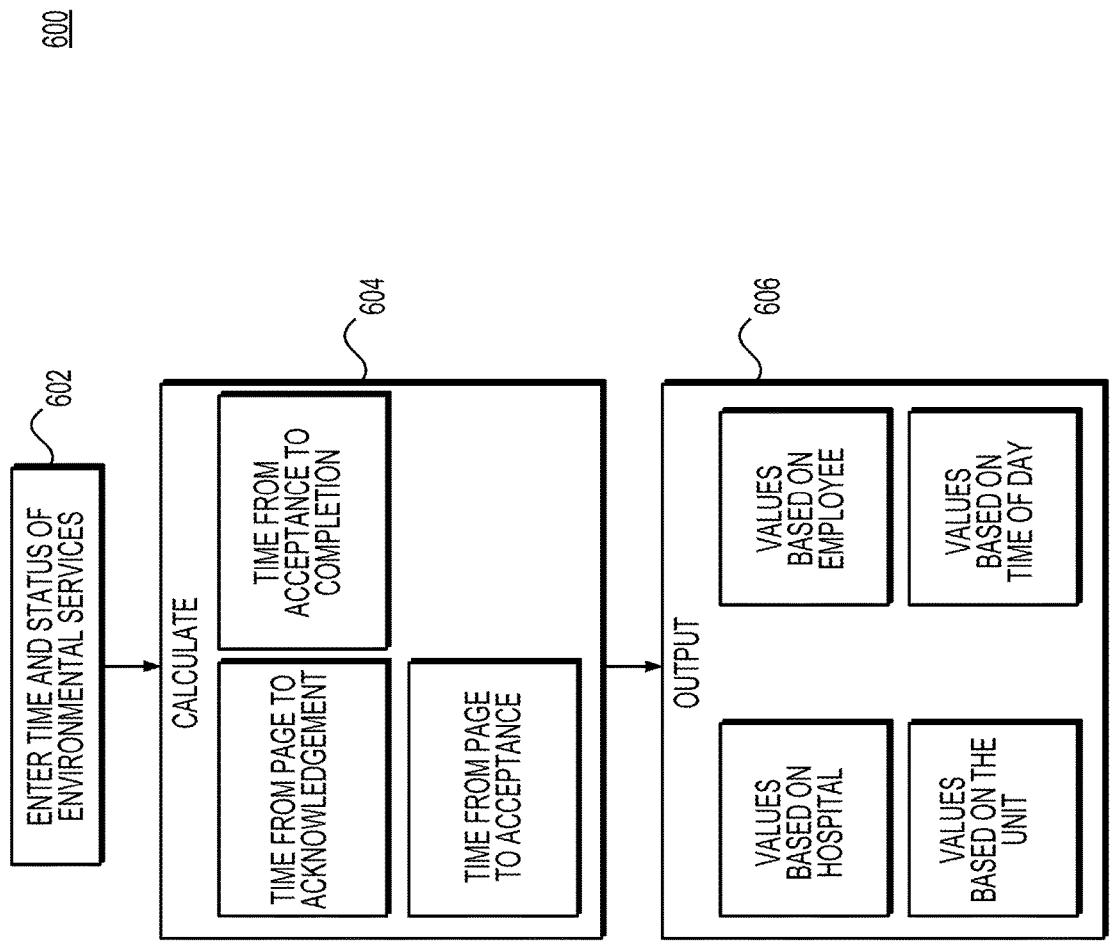
FIG. 6 is a flowchart of an example of a process for determining metrics of the work process, consistent with embodiments of the present disclosure.

FIG. 6 is a flowchart of an example process for measuring, recording, and outputting metrics of a job status. Process 600 is described herein as performed primarily by network server 160, however in some embodiments, facility server 130, computer terminal 140, administration terminal 145, user device 120, and/or third party server 170 may perform one or more steps of process 600. Specifically, in step 602, the events of the job status may be tagged, entered, and recorded by network server 160. Specifically, the time that each event of the job may be tagged according to the type of event (e.g. call, acknowledgement, acceptance, completion), day and time, the employee, the unit, and the hospital. In Step 604, network server 160 may then calculate the time between certain events to take place, such as Time from Page to a Return Call, the Time from Page to Acceptance, and the Time from Acceptance to Completion as depicted in FIG. 6, and tag and record the data accordingly. According to the tagged data, network server 160 may be configured to filter and output the data according to any number of variables in Step 606. For example, network server 160 may be configured to filter and output to determine the time employees of a hospital takes to clean a bed. Network server 160 may also be configured to determine how each employee responds according to each of the criteria. Other determinations may be made including the efficiency of each employee, unit, and/or hospital. Network server 160 is advantageous in that it provides instant feedback of task efficiency and enables the hospital to enhance performance on the employee level, the unit level, the hospital level, and the network level. Network server 160 may also determine the efficiency of the hospital based on the time of day, day of the week, and week of the year. The hospital can staff and operate accordingly to enhance overall efficiency.

FIGS. 7-11 provide illustrations of exemplary interfaces 700, 800, 950, 1000, 1100, consistent with disclosed embodiments. The interfaces may be displayed, for example, at user device 120, computer terminal 140, or administrator terminal 145 based on communication over local network 110 and/or network 150. The interfaces are described herein as performed primarily by processor 220, 330 according to program instructions stored in memory 250, 340, however in some embodiments, facility server 130, computer terminal 140, administration terminal 145, user device 120, and/or third party server 170 may perform one or more steps of the interfaces. The program instructions stored in memory 250, 340 may be customized by adding, subtracting, enlarging, and/or reducing data fields. The data displayed on the interfaces may be received and updated in real time by processors 220, 330 from network server 160, database 180, other computer terminals 140, and/or other user devices 120 located in different hospitals. In some embodiments, the received data may then be stored in memory 250, 340 to be accessed later. Interfaces 700, 800, 900, 1000, 1100 may be organized in a number of different manners, including tabbed browsing as depicted in FIGS. 7-11. The data obtained from the interfaces may be used for processing a transfer request through an operator, or performing automated processes, such as described in processes 500, 600.

Additionally, processor 220, 330 may generate user data based on interaction with user 125. Processor 220, 330 may update the data based on the interaction with user 125 and may transmit this updated data through network 150 to server 160, database 180, other computer terminals 140, and/or other user devices 120. For example, processor 220, 330 may record the date and time that user 125 interacts with the interfaces, and may record receipts and acknowledgements of data (e.g., communications or tasks) based on user 125 viewing the data. Processor 220, 330 may also allow user 125 to directly transmit data by allowing user 125 to generate communications or tasks. This data may be transmitted directly to other computer terminals 140 and/or other user devices 120 to be accessed by other users 125, and/or may be transmitted to server 160 and/or database 180 to update stored data.

Figure 7:
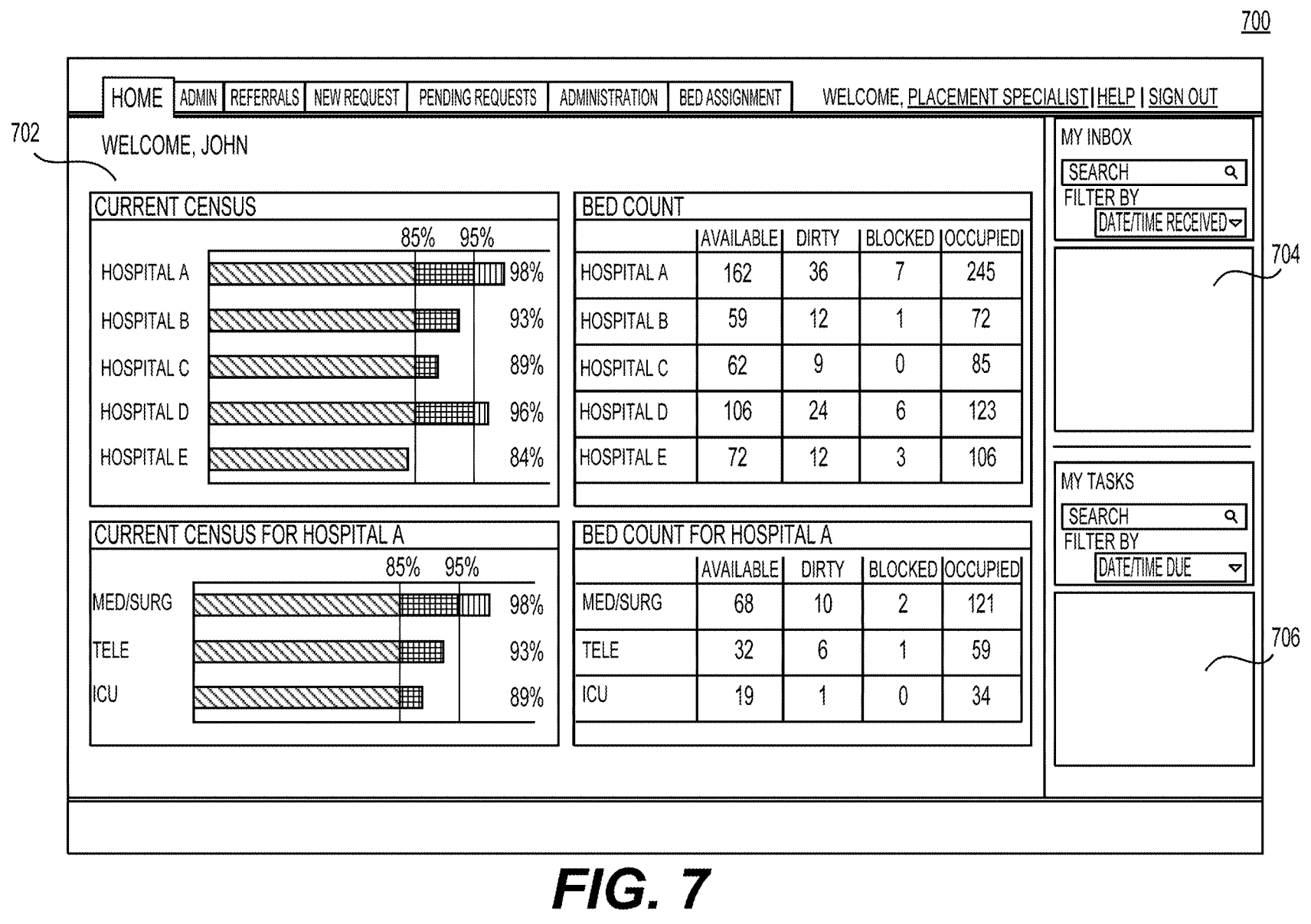

User interface 700, generated by processor 220, 330, may allow users 125, such as an administrator or physician responsible for directing patient placement, to interact with administrator terminal 145 and operate user interface 700. Processor 220, 330 may generate user interface 700 to provide a variety of data without having to search and compare data from different sources. In the embodiment as depicted in FIG. 7, processor 220, 330 may generate a census interface 702 detailing census data of patients at a variety of different units and hospitals, a communication interface 704 that allows communication between user 125 pertaining to possible transfers, and a task interface 706 that details the tasks of the user 125. In some embodiments, the census data, generated by processor, may be displayed in at least one of bar graphs, pie graphs, line graphs, and/or charts. Processor 220, 330 may display the census data according to the quantity of at least one of the available beds, occupied beds, dirty beds, blocked beds, and/or beds with confirmed or pending discharges.

Communication interface 704 may allow communication between users 125 located at hospitals. In particular, processors 220, 330 may allow data to be transmitted between respective user devices 120 and computer terminals 140 via network 150. Network 150 may provide a closed network for the communications, e.g., allowing only limited number of users 125 to send and receive messages through communication interface 704. For example, the limited users 125 may be based on individuals who are responsible for overseeing patient placement and/or who have access to user interface 700. The communications of interface 704 may be sorted and filtered by a number of different properties, such as the status of the communication, the nature of the communication, the date/time sent or received, and the source or recipient of the communication.

Task interface 706 may allow user 125 to view upcoming task. The tasks of interface 706 may be similarly sorted and filtered by a number of properties, such as status of the task, the nature of the task, the date/time sent or received, and the source or recipient of the task. Tasks may be inputted and updated by processor 220, 330 with data received in real time from network server 160, database 180, other computer terminals 140, and/or other user devices 120 located in different hospitals.

Figure 8:
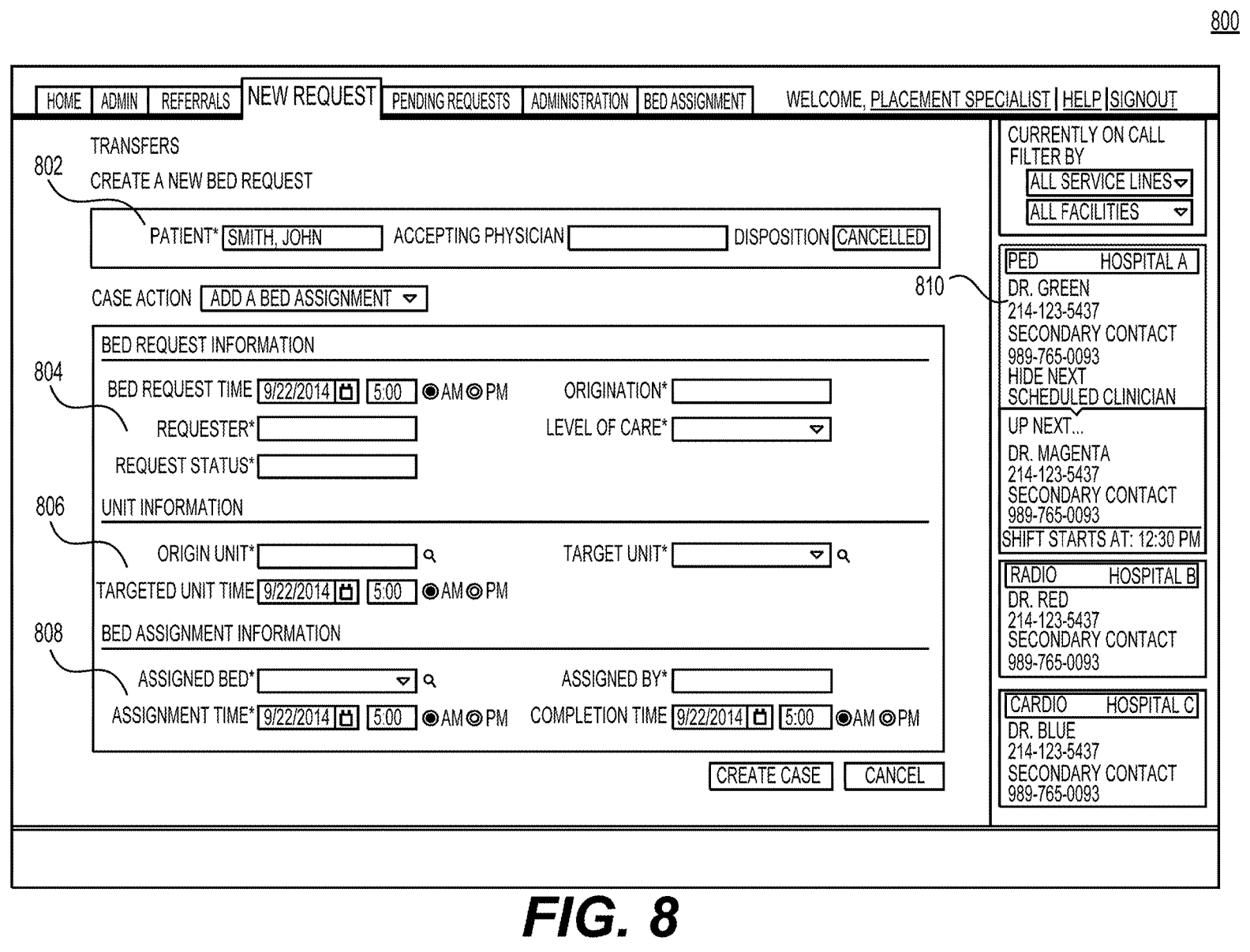

FIG. 8 is an illustration of an example of a patient placement interface 800, consistent with disclosed embodiments. Processor 220, 330 may display patient placement interface 800 in response to a command by user 125 seeking to transfer a patient. After user 125 inputs data pertaining to the patient, processor 220, 330, may generate a data packet for the bed request, and transmit it through network 150 to server 160, database 180, other computer terminals 140, and/or other user devices 120.

Patient placement interface 800 may include a number of different data fields to generate a transfer request. The data fields may include patient information 802, bed request information 804, unit information 806, and bed assignment information 808. Patient information 802 may include data fields for the patient name, the accepting physician, and the disposition. Bed request information 804 may include the bed request time, the requester, the request status, the origination, and the level of care. Unit information 806 may include origin unit, targeted unit time, and targeted unit. Bed assignment information 808 may include the assigned bed, assignment time, assigned by, and completion time. The data inputted in patient placement interface 800 may be used by network server 160 in the processes detailed in FIGS. 5-7.

Processor 220, 330 may also generate and display data in an on-call interface 810. The data may be retrieved by processor 220, 330 through network 150 from server 160, database 180, other computer terminals 140, and/or other user devices 120. Specifically, processor 220, 330 may send a query to server 160, database 180, other computer terminals 140, and/or other user devices 120 to retrieve information pertaining to employees. The information may include names, titles, associated team(s) (e.g., cardiac or trauma), specialties, contact information (e.g., phone numbers and email addresses), and schedules. Processor 220, 330 may then display the information based on criteria input by the user 125. Processor 220, 300 may generate on-call interface 810 in an interactive manner as user 125 inputs data. For instance, as user 125 inputs data for a bed request for a unit (e.g., pediatrics), processor 220, 330 may automatically retrieve and display the employees that may be on-call over a certain period of time in that unit. The data displayed in on-call interface 810 may include information pertaining to physicians on-call at different units and hospitals. On-call interface 810 may allow user 125 to customize the query of processor 220, 330 filtering the data by a variety of different criteria, including unit, campus, and specialty. On-call interface 810 may also provide quick links to contact the on-call physicians in any manner, including email via communication interface 804.

Figure 9:
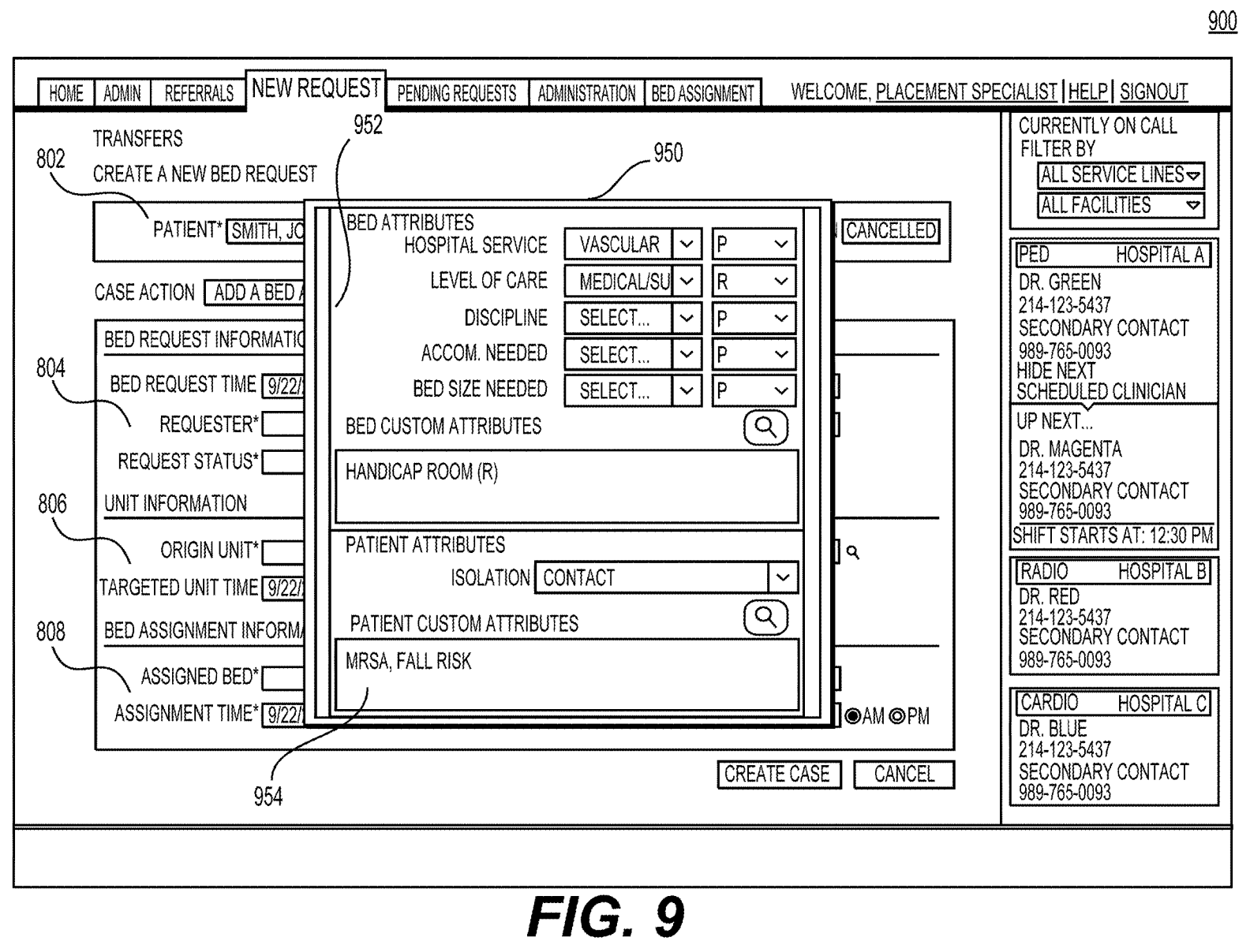

Patient placement interface 800 may allow the user 125 to input additional data pertaining to the patient. FIG. 9 is an illustration of an example of a menu 950, generated by processor 220, 330 consistent with disclosed embodiments. Menu 950 may be displayed by processor 220, 330, when user 125 accesses a displayed hyperlink or button (e.g., "Details" as in FIG. 8). Menu 950 may provide additional fields, for providing information pertaining to the patient that may be utilized in the processes of this disclosure. For example, menu 950 may have data fields 952 for bed attributes and data fields 954 for patient attributes. Data fields 952 may include the requested hospital service, the level of care, the discipline, the accommodations needs, the bed size needed, and bed custom attributes. Data fields 954 may include isolation and patient custom attributes. Data fields 952, 954 may be embodied in either dropdown menus and/or open data fields, as depicted in FIG. 9. In the instance of open data fields, processor 220, 330 may be configured to execute data recognition software (e.g., optical character recognition) in order to extract the data. Processor 220, 330 may request additional data pertaining to each of the data fields 952, 954, including whether each of the fields is critical and a degree of criticality of each of the fields. The data inputted in menu 950 may be used by network server 160 in the processes detailed in FIGS. 5 and 6.

Figure 10:
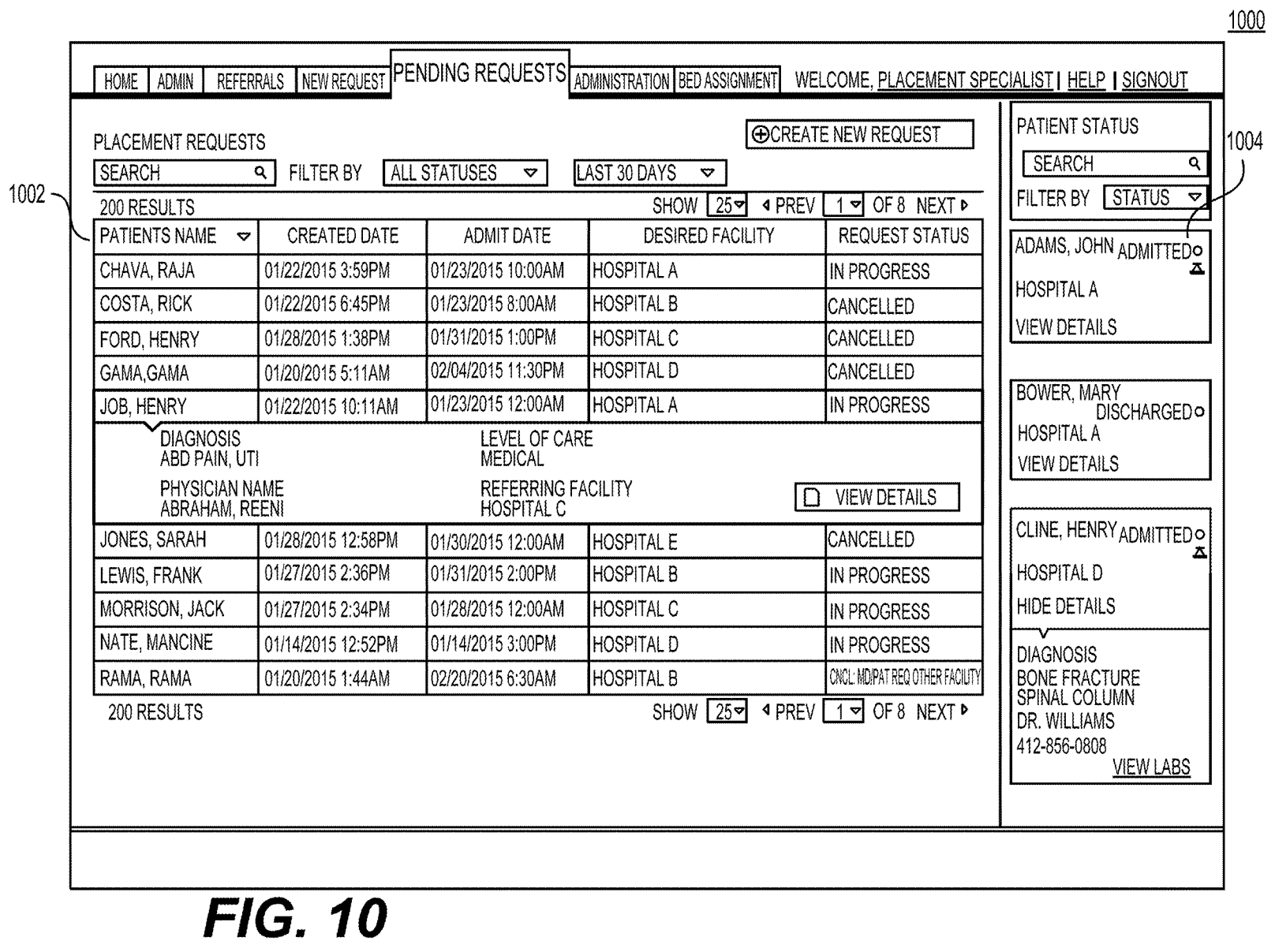

FIG. 10 is an illustration of an example of a patient tracking interface 1000, consistent with disclosed embodiments. In patient tracking interface 1000, processor 220, 330 may retrieve and display data pertaining to statuses of transfer requests. The request statuses may be formatted in a chart 1002 as depicted in FIG. 10, providing information such as patient name, the date the request was created, the date that the patient was admitted, the desired facility, and the request status. A drop-down menu of chart 1002 may provide additional details, such as diagnosis, physician name, level of care, referring facility. Certain transfer statuses may be pinned on patient tracking interface 1000 in a side bar 1004. Transfer requests may be displayed in side bar 1004 when they match any number of criteria. For example, side bar 1004 may display all of the patient transfers requested by user 125. It is also contemplated that side bar 1004 may display only the most recent patient transfers requested by user 125. It is also contemplated that side bar 1004 may display transfer requests user 125 is responsible for receiving.

Figure 11:
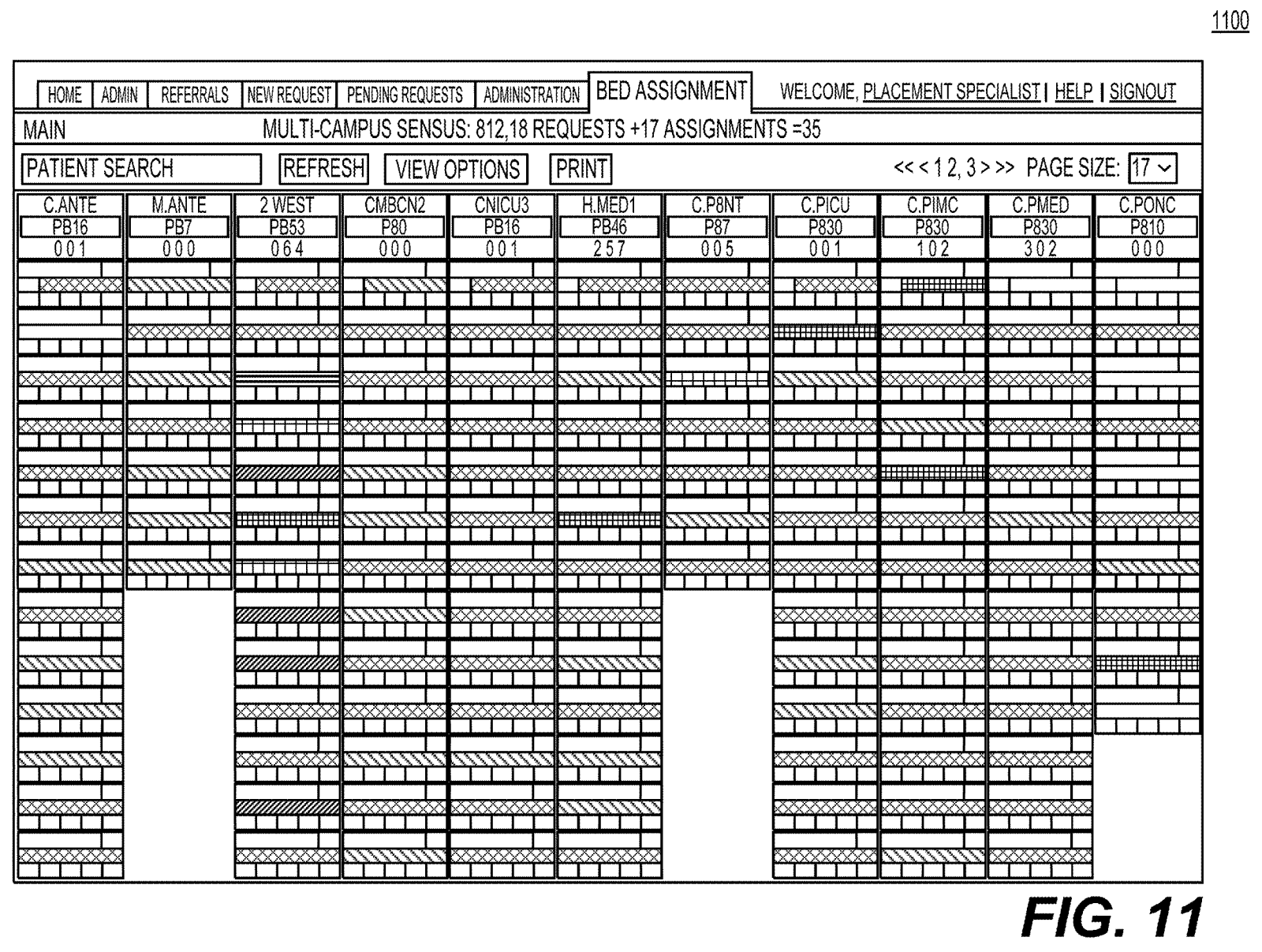

FIG. 11 is an illustration of an example of a bed tracking interface 1100, consistent with disclosed embodiments. In patient tracking interface 1000, processor 220, 330 may retrieve and display data pertaining to bed statuses. Bed tracking interface 1100 may provide the status of beds in any number of manners based on user settings. Bed tracking interface 1100 may display the statuses of beds in at least a portion of a unit. In some embodiments, bed tracking interface 1100 may be configured to provide the statuses of an entire unit and/or hospital. It is also contemplated that bed tracking interface 1100 may display similar units from different hospitals. For each bed displayed, bed tracking interface 1100 may provide information such as the location (e.g., hospital, unit), status, occupying patient, and size. The status of the bed may be selected from at least one of occupied, unoccupied, clean, dirty, pending discharge, scheduled occupant. Processor 220, 330 may generate a color code for each of the bed statuses to provide the user 125 immediate information and additional information may be accessible, for example, by clicking or touching the displayed beds.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A centralized hospital communication server for event monitoring and notification, comprising:
   a memory storing instructions; and
   at least one processor configured to execute the stored instructions to perform operations comprising:
   obtaining real-time occupancy data for a plurality of locations within one or more hospitals, each location associated with at least one location attribute;
   classifying, based on the real-time occupancy data, an availability of each of the locations;
   receiving, from a networked device, (i) event information indicative of an event, the event information comprising attributes of an individual associated with the event, and (ii) priority information indicating relative priorities between at least two of the attributes of the individual, wherein the priority information is based at least in part upon a predetermined hierarchy of importance of the attributes;

identifying, based on the received event information and the received priority information, a selected location for the individual, the selected location being one of the candidate locations having a location attribute that corresponds to an attribute of the individual;

assigning the individual to the selected location;

updating the real-time occupancy data of the selected location based on the assignment;

generating, based on the updated real-time occupancy data, instructions to display a user interface indicating the updated real-time occupancy data on the networked device; and sending, based on the updated real-time occupancy data, a notification to a caregiver device, wherein the notification is acknowledgeable by a user interaction received at the caregiver device.

2. The centralized hospital communication server of claim 1, wherein the real-time occupancy data is obtained from at least one sensor device.

3. The centralized hospital communication server of claim 2, wherein the at least one sensor device comprises an environmental sensor or security sensor.

4. The centralized hospital communication server of claim 1, wherein the priority information indicates whether at least one of the attributes is critical or non-critical.

5. The centralized hospital communication server of claim 1, wherein at least one of the attributes is a physical characteristic of the individual, a preference of the individual, or isolation information.

6. The centralized hospital communication server of claim 1, the operations further comprising receiving an electronic record comprising additional attributes of the individual, wherein the identifying is based on the additional attributes.

7. The centralized hospital communication server of claim 1, wherein at least one of the availabilities is an unavailability comprising an indication of expected availability within a predetermined time period.

8. The centralized hospital communication server of claim 7, wherein the indication is based on a scheduled event.

9. The centralized hospital communication server of claim 1, wherein at least one of the location attributes comprises information associated with a bed at one of the locations.

10. The centralized hospital communication server of claim 1, wherein assigning the individual to the selected location is based on a manual bed request.

11. The centralized hospital communication server of claim 1, wherein at least one of the event information or priority information is received in response to a request provided at a user interface.

12. The centralized hospital communication server of claim 11, wherein the user interface includes fields designated as critical or non-critical.

13. The centralized hospital communication server of claim 11, wherein the request comprises a requested unit within a requested hospital.

14. The centralized hospital communication server of claim 13, wherein identifying the selected location comprises a physical proximity of the selected location to the requested unit.

15. The centralized hospital communication server of claim 1, wherein the individual is a first individual and identifying the selected location is based on at least one attribute of a second individual.

16. A centralized hospital communication method for event monitoring and notification, performed by a centralized communication server, and comprising:

obtaining real-time occupancy data for a plurality of locations within one or more hospitals, each location associated with at least one location attribute;

classifying, based on the real-time occupancy data, an availability of each of the locations;

receiving, from a networked device, (i) event information indicative of an event, the event information comprising attributes of an individual associated with the event, and (ii) priority information indicating relative priorities between at least two of the attributes of the individual, wherein the priority information is based at least in part upon a predetermined hierarchy of importance of the attributes;

identifying, based on the received event information and the received priority information, a selected location for the individual, the selected location being one of the candidate locations having a location attribute that corresponds to an attribute of the individual;

assigning the individual to the selected location;

updating the real-time occupancy data of the selected location based on the assignment;

generating, based on the updated real-time occupancy data, instructions to display a user interface indicating the updated real-time occupancy data on the networked device; and sending, based on the updated real-time occupancy data, a notification to a caregiver device, wherein the notification is acknowledgeable by a user interaction received at the caregiver device.

17. The centralized hospital communication method of claim 16, wherein at least one of the attributes is a physical characteristic of the individual, a preference of the individual, or isolation information.

18. The centralized hospital communication method of claim 16 further comprising receiving an electronic record comprising additional attributes of the individual, wherein the identifying is based on the additional attributes.

19. The centralized hospital communication method of claim 16, wherein at least one of the availabilities is an unavailability comprising an indication of expected availability within a predetermined time period.

20. The centralized hospital communication method of claim 19, wherein the indication is based on a scheduled event.

* * * * *